United States Patent [19]

Kissinger

[11] Patent Number: 5,434,316
[45] Date of Patent: Jul. 18, 1995

[54] PURIFICATION OF BISPHENOL-A

[75] Inventor: Gaylord M. Kissinger, Evansville, Ind.

[73] Assignee: General Electric Company, Pittsfield, Mass.

[21] Appl. No.: 281,970

[22] Filed: Jul. 28, 1994

[51] Int. Cl.⁶ ............................................. C07C 37/84
[52] U.S. Cl. .................................. 568/724; 568/722; 568/727; 568/728; 422/245.1; 422/255
[58] Field of Search ............... 568/722, 724, 727, 728; 423/584

[56] References Cited

U.S. PATENT DOCUMENTS

| | | |
|---|---|---|
| 3,326,986 | 6/1967 | Doggan et al. ...................... 568/724 |
| 4,927,973 | 5/1990 | Dong et al. .......................... 568/724 |
| 5,243,093 | 9/1993 | Kissinger et al. .................... 568/724 |
| 5,300,700 | 4/1994 | Malamet et al. ..................... 568/724 |
| 5,345,000 | 9/1994 | Moriya et al. ....................... 568/724 |

OTHER PUBLICATIONS

Kokai Japanese Patent Application No. HEI 5 (1993)-97746.
Kokai Japanese Patent Application No. HEI 5 (1993)-97744.

*Primary Examiner*—Werren B. Lone

[57] ABSTRACT

Bisphenol-A produced by the condensation of acetone and phenol is freed of contaminant co-products by melting and crystallization in and from water. The final washing, in hot water, cleanses the crystal surfaces of remaining contaminants without the need for organic solvents.

20 Claims, 1 Drawing Sheet

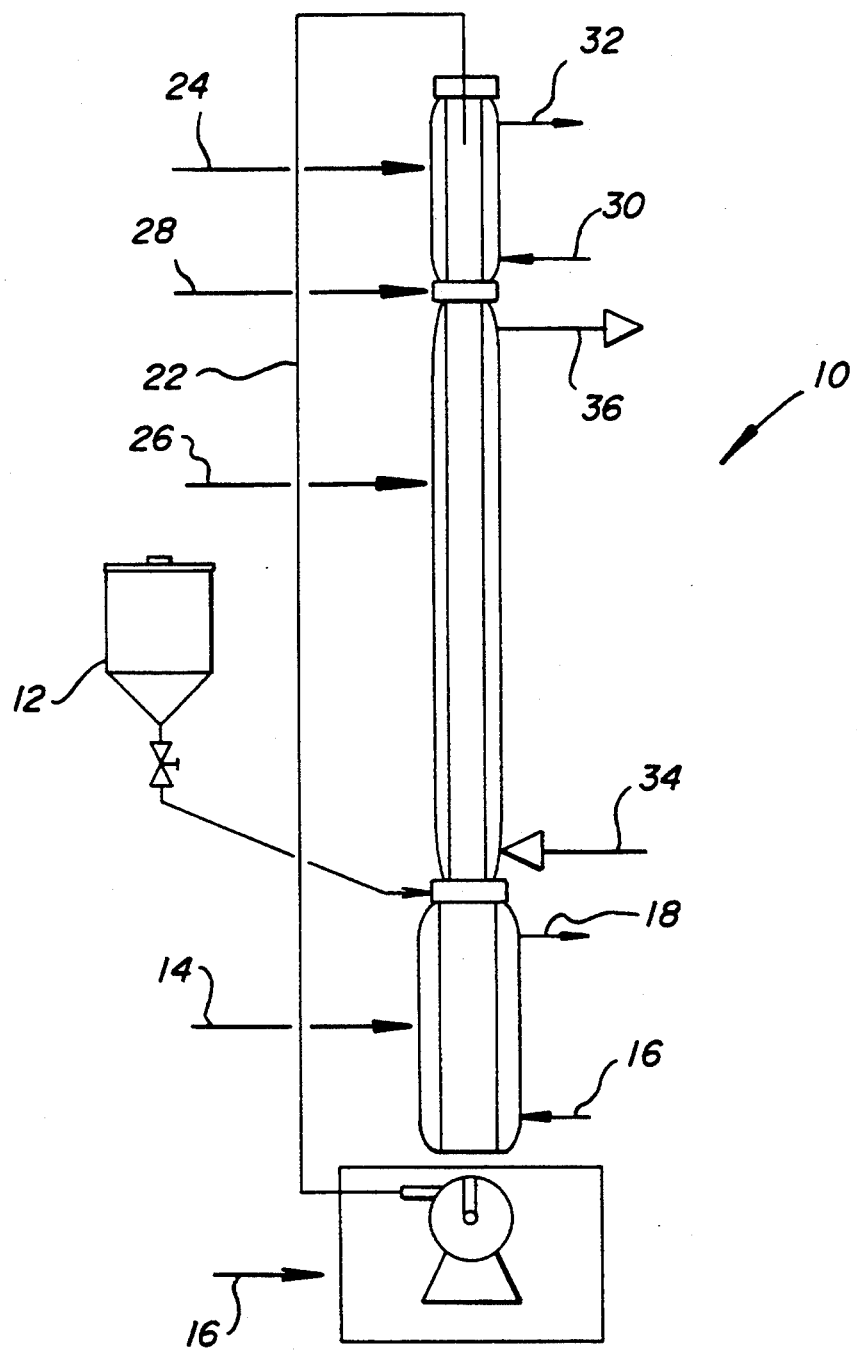

PURIFICATION OF BISPHENOL-A

BACKGROUND OF THE INVENTION

1. Field of The Invention

The invention relates to methods and procedures for the purification of bisphenol-A, and more particularly relates to purification by recrystallization from aqueous dispersions.

2. Brief Description of Related Art

Bisphenol-A [2,2-bis (4'-hydroxyphenyl)propane] is a valuable aromatic compound produced commercially by the reaction of a stoichiometric excess of phenol with acetone. In the course of manufacture, the desired bisphenol-A is precipitated as a crystalline adduct with unreacted phenol, including contaminant by-products and color bodies. Purification is desirable for many uses of the bisphenol-A, where the phenol and other contaminants would be objectionable.

Numerous purification procedures have been postulated and practiced to obtain bisphenol-A of high purity. Representative of such procedures are those described in the Japanese KOKAI PATENT APPLICATION NO. HEI 5[1993]-97746. According to this reference, the bisphenol-A/phenol adduct initially precipitated can be purified through a multi-stage crystallization procedure, interspersed with melting and separations. The reference teaches that such multi-stage recrystallizations do not completely remove substances that cause color, and the product crystals are still colored and not acceptable for all uses. The reference teaches washing the wet cake of powdered adduct with an organic solvent for phenol at a temperature of 60°–120° C., removing adsorbed solvent and drying the cake.

The multi-stage crystallizations as taught in U.S. Pat. No. 524,309 collectively referred to in the artisans language, as "melt crystallization" is a multi-stage purification process. The impurity "distribution coefficient" or "separation factor" achieved during each stage of separation is critical in determining the number of separation stages required to reach the desired product purity.

The present invention offers a process with an impurity "separation factor" greater than the prior art Melt Crystallization process, resulting in a process which achieves the desired purity in fewer stages.

Additionally, the temperatures at which this new purification process are carried out are significantly lower than those required in the prior art Melt Crystallization process. This fact, along with the potential for reducing energy consumption, makes it possible to substitute water and steam alternately, as the Heat Transfer Medium (HTM) in place of Therminol or Dowtherm type oils. These oils are very expensive, are environmentally troublesome, and are toxic to the waste water treatment Biomass.

The process of the invention produces a highly purified bisphenol-A in a high first pass yield, without the need for distillation, slurry handling, rotary vacuum filters, centrifuges, or the use of organic solvents.

The lower process temperatures employed in the process of the invention are due to the fact that bisphenol-A is first saturated with water. Bisphenol-A in relatively pure form occurs as crystals or flakes with a melting point (solidification range) of from about 150° to 155° C. The solid is practically insoluble in water.

However, in the presence of at least an equimolar proportion of water (7.3 percent by weight) the melting point of bisphenol-A is lowered to about 96° C. At this temperature, the bisphenol-A forms an "oil" which is heavier than and also immiscible with water. A separate layer does not form in the mixture however, until the water saturation level is exceeded.

Advantageously, the amount of water included in the mixture with the "oil" or melted bisphenol-A is within the range of from about 20 percent by weight to 60 percent by weight of the total mixture, preferably 30 to 50 percent. The bisphenol-A/water "oil" can be maintained at a temperature of circa 98° C. under atmospheric pressures (preferably at an elevated pressure of circa 1 to 10 PSIG).

Cooling of this mixture of essentially immiscible phases, with vigorous agitation, results in the formation of orthorhombic crystals of BPA which can be separated on a filter. The impurity laden fraction, which has been separated from the BPA is deposited as a "tacky" viscous "oil" on the surfaces of the BPA crystals. This is the basis of another purification procedure (described in the U.S. Pat. No. 3,326,986) where an organic solvent is used to wash the crystal cake, to solubilize the viscous coating of impurities. The process requires an organic solvent wash, the use of filters, centrifuges, slurry handling, and drying. Many of these steps and solvents are avoided by the improved process of the present invention.

SUMMARY OF THE INVENTION

The invention comprises, a process for the purification of bisphenol-A by separating contaminants associated with the compound when prepared by the condensation of phenol with acetone in the presence of an acid catalyst, which comprises;

A. melting the contaminated bisphenol-A compound in an aqueous mixture;

B. crystallizing bisphenol-A from the aqueous mixture;

C. separating the crystals from the resulting aqueous mixture; and

D. washing the crystals with water at a temperature of from about 35° C. to below the melting point of the crystals.

The process of the invention can be carried out continuously or in batchwise procedures. As will be appreciated, lower temperatures, elimination of heat transfer fluids, and fewer purification stages are required when compared to the prior art Fractional Melt Crystallization process.

Fewer stages with higher separation factors, and elimination of the need for heat transfer oils are economic advantages. The lower process temperatures reduces the thermal oxidative degradation of the bisphenol-A, improving the product.

BRIEF DESCRIPTION OF THE DRAWING

The drawing is a schematic view of embodiment apparatus of the invention for carrying out the process of the invention.

DETAILED DESCRIPTION OF THE PREFERRED EMBODIMENTS OF THE INVENTION

Those skilled in the art will gain an appreciation of the invention from a viewing of the accompanying drawing in conjunction with a reading of the following description of preferred embodiments of the invention.

Referring first to the drawing, a process of the invention will be described. The drawing is a schematic depiction of apparatus 10 for the purification of bisphenol-A (hereinafter referred to at times for convenience as "BPA"). Melted and water-saturated bisphenol-A (at a temperature of circa 98° C. to 105° C.), preferably under a slight pressure as aforementioned is delivered from a feed tank 12 to a sump tank 14 which is jacketed and heated through circulating hot fluid carried in by conduit 16 and out by conduit 18. The mixed water and organic phases are maintained in sump tank 14 at a temperature of 90° to 105° C.

After the liquified BPA and water phases are charged to the sump tank 14, the product circulation pump 16 is started, and liquid containing both phases, but primarily the organic phase, is pumped through a temperature controlled feed pipe 22 to the head tank 24 at the top of the crystallizer column 26.

The liquid being pumped into the head tank 24 flows down through a feed distributor 28 located between the head tank 24 and crystallizer column 26 and is caused to run down the inside wall of the crystallizer column 26 as a liquid "film".

The product circulation pump 16, the sump tank 14, the feed pipe 22, and the head tank 24 are all temperature controlled slightly above the crystallizing temperature of the liquid (control not shown). The head tank 24 is jacketed and heated by fluid circulated through conduits 30,32.

The crystallizer column 26, however, with the liquid film flowing down the inside wall, has its's temperature held at a constant level 1 or 2 degrees C. below its saturation temperature until crystal nuclei, or "seeds" form on the tube wall. This temperature is controlled and maintained by circulating a hot fluid through conduits 34,36 into a jacket on crystallizer column 26. After seeds are present on the tube wall, the temperature is ramped downward slowly at a controlled rate of from about 0.01° to about 1.0° C./min. This ramping down of the temperature brings about the continued saturation of the liquid phase, in which BPA is the predominant component. Highly purified orthorhombic crystals of BPA are continually grown larger and more numerous until a point is reached where the remaining BPA is "soluble" in the liquid phase, and regardless of any further lowering of the temperature, will no longer saturate and form crystals on the wall of the crystallizer column 26. It is a falling film crystallization.

At this point, the pumping action is stopped, and the remaining organic residue is drained away, to be stripped of residual water, and recycled for recovery of residuals.

After the residue is drained away, the water phase remains in the sump tank 14 and the BPA crystals are still attached to the crystallizer column 26 wall.

The water phase is heated slightly to a temperature of circa 95° C., the circulation pump 16 is started, and water phase is pumped to the head tank 20 from which it flows downward over the crystal cake still attached to the wall of column 26. This action of flowing the hot water over the crystals, lowers the viscosity of the impure residue which is adhering to the surfaces of the BPA crystals, causing it to accumulate in the sump tank 14 below. After the hot water flushing operation, additional residue can be decanted from below the water phase, which is still contained in the sump tank 14.

If desired, the original or a fresh water phase can be circulated across the surface of the BPA crystals in subsequent cycles, while raising the temperature high enough to bring about the complete remelting of the crystalline product from the wall of recrystallizer column 26. At this point, a second or more crystallization cycles can be performed according to the same principle as the first. The crystals are in subsequent repeat cycles from a BPA/water/impurity system which is much reduced in impurity content, due to the prior removal of the impurities concentrated in the residue following the first or previous crystallizing cycles, resulting in very highly purified BPA product.

When ultrapurity is desired, the BPA crystals produced by the process of the invention may be further purified by conventional crystallization processes such as the prior art Melt Crystallization procedures.

The following examples and preparations describe the manner and process of carrying out the invention and set forth the best mode contemplated by the invention. In the following examples, the apparatus 10 described above was employed.

EXAMPLE 1

400 grams of crude BPA feed was added along with 250 grams of water to the crystallizer sump tank. The tracing oil on the sump tank (14), the feed line (22), and the head tank (24), was controlled at a temperature of around 97–99 degrees C.

The circulation pump (16), was started, and feed material pumped to the head tank (24), from which it flowed by gravity downward through the feed distributor (28), and along the walls of the crystallizer (26). The crystallizer oil temperature was controlled initially at about 88–90 degrees C.

Nucleation of the BPA occurred at around 94–95 degrees C., which was a measure of the actual product feed temperature.

Following nucleation, the crystallizer oil temperature was ramped downward at a rate of about 0.05 degrees C./minute. This action was continued until the product feed temperature was reduced (by the cooling effect of the crystallizer wall) to around 91–93 degrees C.

At this point, no further reduction in the level of the sump tank (14) was observed, and the pumping action was stopped. After a few minutes, the decanted organic residue was drained from the bottom of sump tank (14).

After the organic phase had been drained, the water phase was now circulated to the top of the crystallizer, and allowed to flow down across the surface of the crystals attached to the crystallizer wall. After several minutes, the pump was stopped, and additional residue was decanted and combined with the original residue. The water phase was then drained from the sump tank (14). The crystallizer oil temperature was now raised slowly to a maximum of about 155 degrees C., and sweat liquor was collected in the sump tank (14). After the sweat liquor was drained from the sump tank (14), the temperature was raised immediately to about 175 degrees C. This resulted in the melting of the crystals. The Melt was collected, weighed and analyzed by Liquid Chromatography, along with the sweat and residue liquors.

The analytical results from the crude feed, residue, sweat and product are shown below in Table 1.

TABLE 1

| WEIGHT % | CRUDE FEED | RESIDUE | SWEAT | PRODUCT MELT |
|---|---|---|---|---|
| phenol | 0.57 | 1.27 | 0.62 | NDA |

TABLE 1-continued

| WEIGHT % | CRUDE FEED | RESIDUE | SWEAT | PRODUCT MELT |
| --- | --- | --- | --- | --- |
| IPP | 0.04 | 0.02 | 0.04 | 0.001 |
| p,p' BPA | 89.67 | 79.03 | 92.74 | 99.88 |
| o,p' BPA | 3.76 | 8.54 | 3.39 | 0.07 |
| IPP Dimers | 0.67 | 0.69 | 0.33 | 0.005 |
| BPX-I | 0.71 | 1.76 | 0.75 | 0.009 |
| Chroman | 1.36 | 1.49 | 0.43 | 0.007 |
| spiro-biindane | 0.003 | 0.04 | NDA | NDA |
| BPX-II | 2.07 | 4.20 | 0.69 | 0.011 |
| Unknowns | 1.16 | 2.96 | 1.01 | 0.018 |
| Grams (*) | 400.00 | 41.45 | 156.35 | 128.20 |

(*) Note: Balance of organic material was separated in the water phase.

EXAMPLE 2

Following the general procedures of Example 1, supra, but starting with 300 grams of BPA crude feed and 200 grams of water, the analytical results are shown in Table 2, below.

TABLE 2

| WEIGHT % | CRUDE FEED | RESIDUE | SWEAT | PRODUCT MELT |
| --- | --- | --- | --- | --- |
| phenol | 0.57 | 1.39 | 0.09 | 0.01 |
| IPP | 0.04 | 0.05 | 0.03 | 0.001 |
| p,p' BPA | 89.67 | 68.89 | 78.86 | 97.66 |
| o,p' BPA | 3.76 | 15.13 | 10.82 | 1.37 |
| IPP Dimers | 0.67 | 1.44 | 1.03 | 0.10 |
| BPX-I | 0.71 | 4.80 | 3.44 | 0.21 |
| Chroman | 1.36 | 4.07 | 2.74 | 0.16 |
| spiro-biindane | 0.003 | 1.09 | 0.71 | NDA |
| BPX-II | 2.07 | 1.74 | 1.23 | 0.10 |
| Unknowns | 1.16 | 1.35 | 1.01 | 0.39 |
| Grams (*) | 300.00 | 62.59 | 28.60 | 157.00 |

(*) Note: Balance of organic material was separated in the water phase.

EXAMPLE 3

Following the general procedure of Example 1, supra but starting with 400 gms of BPA or crude feed and 400 gms of water, the analytical results are shown in Table 3 below.

TABLE 3

| WEIGHT % | CRUDE FEED | RESIDUE (*) | SWEAT (*) | PRODUCT MELT |
| --- | --- | --- | --- | --- |
| phenol | 0.99 | | | NDA |
| IPP | 0.07 | | | NDA |
| p,p' BPA | 88.15 | | | 99.15 |
| o,p' BPA | 4.06 | | | 0.48 |
| IPP Dimers | 1.71 | | | 0.16 |
| BPX-I | 0.65 | | | 0.04 |
| Chroman | 1.08 | | | 0.05 |
| spiro-biindane | NDA | | | NDA |
| BPX-II | 1.32 | | | 0.02 |
| Unknowns | 1.97 | | | 0.10 |
| Grams (**) | 400.00 | 41.45 | 156.35 | 151.63 |

Notes: (*) Did not analyze Residue and Sweat Compositions
(**) Balance of organic material was separated in the water phase.

IN THE TABLES 1-3

NDA is "No Detectable Amount"
IPP is isopropenylphenol
IPP Dimers are dimers of isopropenylphenol
p,p' BPA is bisphenol-A (BPA)
o,p' BPA is ortho-para bisphenol-A
BPX-I and BPX-II are trisphenols
Chroman is chroman-1
"Unknowns" are unknown impurities detectable by Liquid Chromatography

I claim:
1. A process for the purification of bisphenol-A by separating contaminants associated with the compound when prepared by the condensation of phenol with acetone in the presence of an acid catalyst, which comprises;
   A. melting the contaminated bisphenol-A compound in an aqueous mixture;
   B. crystallizing bisphenol-A from the aqueous mixture;
   C. separating the crystals from the resulting aqueous mixture; and
   D. washing the crystals with water at a temperature of from about 35° C. to below the melting point of the crystals.
2. The process of claim 1 wherein the bisphenol-A is melted with water, the proportion of water comprising from 20 to 60 percent by weight of the aqueous mixture.
3. The process of claim 2 wherein the proportion of water comprises from 30 to 50 percent by weight of the aqueous mixture.
4. The process of claim 1 wherein the wash water is at a temperature of from about 90° to about 155° C.
5. The process of claim 4 wherein the wash water is at a temperature or about 95° C.
6. The process of claim 1 carried out continuously.
7. The process of claim 1 which further comprises melting the washed crystals with water at a temperature above the melting point of the crystals.
8. The process of claim 7 wherein the water used to melt the washed crystals is the wash water used from washing said crystals.
9. The process of claim 8 carried out repetitively in a plurality of cycles of the steps B-D.
10. The process of claim 8 wherein the temperature of the wash water used to melt the crystals is at about 155° C.
11. A process for the removal of contaminants associated with bisphenol-A prepared by the condensation of acetone with phenol in the presence of an acid catalyst, from the bisphenol-A, which comprises;
   A. melting the bisphenol-A in an aqueous mixture, at a temperature within the range of from about 95° to 100° C. under atmospheric pressure;
   B. crystallizing the bisphenol-A from the aqueous mixture, whereby a mother liquor remains, comprising water and organics; separating the crystals from the mother liquor;
   C. separating water from the mother liquor; and
   D. washing the crystals with the water separated from the mother liquor, at a temperature above room temperature but below the melting point of the crystals.
12. The process of claim 11 wherein the bisphenol-A is melted with water, the proportion of water comprising from 20 to 60 percent by weight of the aqueous mixture.
13. The process of claim 12 wherein the steps A-D are carried out a plurality of times in sequence.
14. The process of claim 13 wherein the number of times is 2.
15. A process for removing the by-product contaminants of a procedure for the preparation of bisphenol-A by condensation of acetone with phenol, from the bisphenol product, which comprises;
   A. melting the bisphenol-A product in an aqueous medium at a temperature of about 95° to 100° C. under atmospheric pressures;
   B. crystallizing bisphenol-A from the aqueous medium, the residue medium containing organics and water;

C. separating the water from the residue medium;
D. melting the bisphenol-A crystals in water, whereby an aqueous mixture is formed;
E. crystallizing bisphenol-A from the aqueous mixture formed in step D; and
F. separating the bisphenol-A crystals from the aqueous mixture resulting in step E.

16. The process of claim 15 wherein the water in which the bisphenol-A crystals are melted in step (D) is fresh water.

17. The process of claim 15 wherein the water in which the bisphenol-A crystals are melted in step (D) is the water separated from the residue in step (C).

18. The process of claim 15 wherein the melting in step (C) is at a water temperature of about 155° C. under atmospheric pressure.

19. The process of claim 15 carried out by repetition of steps A–F a plurality of times in sequence.

20. Apparatus for the removal of by-product contaminants from bisphenol-A prepared by condensation of acetone with phenol in the presence of an acid catalyst, which comprises;
a vertically disposed crystallizer column having an open top end and an open bottom end;
means on the exterior of the column for controlling temperature in the column;
a supply vessel mounted on the open top end of the column;
pump means connected by a conduit to the supply vessel;
a sump tank mounted on the open bottom end of the column;
a feed conduit for feeding the contaminated bisphenol-A to the sump tank; and
a conduit between the sump-tank and the pump means for circulating bisphenol-A from the sump tank.

* * * * *